(12) United States Patent
Zucker et al.

(10) Patent No.: US 11,696,788 B2
(45) Date of Patent: Jul. 11, 2023

(54) SHAPER FOR VERTEBRAL FIXATION RODS

(71) Applicant: MAZOR ROBOTICS LTD., Caesarea (IL)

(72) Inventors: Edo Zucker, Tel Aviv (IL); Moshe Shoham, Hoshaya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 609 days.

(21) Appl. No.: 16/726,720

(22) Filed: Dec. 24, 2019

(65) Prior Publication Data
US 2020/0129217 A1 Apr. 30, 2020

Related U.S. Application Data

(63) Continuation of application No. 15/533,037, filed as application No. PCT/IL2015/051182 on Dec. 4, 2015, now Pat. No. 10,631,907.
(Continued)

(51) Int. Cl.
*A61B 17/88* (2006.01)
*B21D 7/12* (2006.01)
(Continued)

(52) U.S. Cl.
CPC ........ *A61B 17/8863* (2013.01); *A61B 5/0036* (2018.08); *A61B 5/107* (2013.01);
(Continued)

(58) Field of Classification Search
None
See application file for complete search history.

(56) References Cited

U.S. PATENT DOCUMENTS

| 5,343,385 A | 8/1994 | Joskowicz et al. |
| 5,992,210 A | 11/1999 | Blurton-Jones |

(Continued)

FOREIGN PATENT DOCUMENTS

| CN | 102300512 | 12/2011 |
| CN | 105078577 | 11/2015 |

(Continued)

OTHER PUBLICATIONS

International Search Report and Written Opinion for International (PCT) Patent Application No. PCT/IL2015/051182, dated Mar. 16, 2016, 8 pages.
(Continued)

*Primary Examiner* — Yi-Shan Yang
(74) *Attorney, Agent, or Firm* — Sheridan Ross P.C.

(57) ABSTRACT

A system for rod bending for use in robotic spinal surgery, enabling the correct bending of a fusion rod to match the shape required to accurately pass through the heads of the pedicle screws. The system uses data generated by information provided to the robot by the surgeon's preoperative plan, optionally augmented by feedback from the robot control system of deviations encountered intraoperatively. Such deviations could occur, for example, when the surgeon decides intraoperatively on a different trajectory or even to skip screws on one vertebra, in which case, the robot will be commanded to perform the alternative procedure, with commensurate instructions relayed to the control system of the rod-bending machine. The system is also able to thin down the rod at predetermined locations along its length, adapted to be at selected intervertebral locations, for maintaining limited flexibility between vertebrae, instead of fixating them.

17 Claims, 3 Drawing Sheets

Related U.S. Application Data

(60) Provisional application No. 62/087,314, filed on Dec. 4, 2014.

(51) Int. Cl.

| | | |
|---|---|---|
| *B21D 7/14* | (2006.01) | |
| *A61B 5/00* | (2006.01) | |
| *A61B 5/107* | (2006.01) | |
| *A61B 34/10* | (2016.01) | |
| *A61B 17/70* | (2006.01) | |
| *A61B 17/00* | (2006.01) | |

(52) U.S. Cl.
CPC ............ *A61B 34/10* (2016.02); *B21D 7/12* (2013.01); *B21D 7/14* (2013.01); *A61B 17/70* (2013.01); *A61B 17/7002* (2013.01); *A61B 2017/00526* (2013.01); *A61B 2034/108* (2016.02)

(56) References Cited

U.S. PATENT DOCUMENTS

| | | | |
|---|---|---|---|
| 6,035,691 A * | 3/2000 | Lin .................. | B21D 7/06 72/308 |
| 6,235,028 B1 | 5/2001 | Brumfield et al. | |
| 6,253,595 B1 | 7/2001 | Lewis, Jr. | |
| 7,815,664 B2 | 10/2010 | Sherman et al. | |
| 8,002,798 B2 | 8/2011 | Chin et al. | |
| 8,177,817 B2 | 5/2012 | Fallin | |
| 8,549,888 B2 | 10/2013 | Isaacs et al. | |
| 8,607,603 B2 | 12/2013 | Justis et al. | |
| 8,845,649 B2 | 9/2014 | Jackson | |
| 8,894,655 B2 | 11/2014 | Fallin | |
| 8,979,862 B2 | 3/2015 | Barry et al. | |
| 9,003,859 B2 | 4/2015 | Paris et al. | |
| 9,039,772 B2 | 5/2015 | Park et al. | |
| 9,173,692 B1 | 11/2015 | Kaloostian | |
| 9,271,857 B2 | 3/2016 | Pool et al. | |
| 9,398,925 B2 | 7/2016 | Kiester | |
| 9,421,596 B2 | 8/2016 | Paris et al. | |
| 9,439,692 B1 | 9/2016 | Schlesinger et al. | |
| 9,636,162 B2 | 5/2017 | Isaacs | |
| 9,730,739 B2 | 8/2017 | Taylor et al. | |
| 10,070,936 B2 | 9/2018 | Fallin | |
| 10,136,929 B2 | 11/2018 | Fallin et al. | |
| 10,188,480 B2 | 1/2019 | Scholl et al. | |
| 10,194,957 B2 | 2/2019 | Rouge et al. | |
| 10,194,968 B2 | 2/2019 | Crawford et al. | |
| 10,390,884 B2 | 8/2019 | O'Neil et al. | |
| 10,396,173 B2 | 8/2019 | Rogers et al. | |
| 10,398,481 B2 | 9/2019 | Goel et al. | |
| 10,405,908 B2 | 9/2019 | Redmond | |
| 10,405,935 B2 | 9/2019 | McGahan et al. | |
| 10,433,893 B1 | 10/2019 | Scholl et al. | |
| 10,449,006 B2 | 10/2019 | Dace | |
| 10,492,838 B2 | 12/2019 | Fallin et al. | |
| 2003/0004512 A1 | 1/2003 | Farris et al. | |
| 2003/0055435 A1 | 3/2003 | Barrick | |
| 2005/0033291 A1 | 2/2005 | Ebara | |
| 2005/0085714 A1 | 4/2005 | Foley et al. | |
| 2005/0240078 A1 | 10/2005 | Kwon et al. | |
| 2005/0262911 A1* | 12/2005 | Dankowicz ........ | A61B 17/8863 72/31.04 |
| 2006/0009775 A1 | 1/2006 | Dec et al. | |
| 2006/0074418 A1 | 4/2006 | Jackson | |
| 2006/0150698 A1 | 7/2006 | Garner et al. | |
| 2006/0150699 A1 | 7/2006 | Garner et al. | |
| 2008/0125780 A1 | 5/2008 | Ferree | |
| 2008/0154120 A1 | 6/2008 | von Jako et al. | |
| 2009/0254326 A1 | 10/2009 | Isaacs | |
| 2010/0042154 A1 | 2/2010 | Biedermann et al. | |
| 2010/0152740 A1 | 6/2010 | O'Reilly et al. | |
| 2010/0222822 A1 | 9/2010 | Farris et al. | |
| 2010/0318130 A1 | 12/2010 | Parlato et al. | |
| 2011/0077690 A1 | 3/2011 | Shin et al. | |
| 2011/0270262 A1* | 11/2011 | Justis ................ | A61B 17/8863 606/101 |
| 2012/0186411 A1 | 7/2012 | Lodahi et al. | |
| 2012/0232339 A1 | 9/2012 | Csiky | |
| 2013/0090692 A1 | 4/2013 | Nuckley et al. | |
| 2013/0345757 A1 | 12/2013 | Stad | |
| 2014/0137618 A1 | 5/2014 | Isaacs | |
| 2014/0303672 A1 | 10/2014 | Tran et al. | |
| 2014/0316420 A1 | 10/2014 | Ballard et al. | |
| 2015/0100091 A1 | 4/2015 | Tohmeh et al. | |
| 2015/0196365 A1 | 7/2015 | Kostrzewski et al. | |
| 2015/0305786 A1 | 10/2015 | Wehrle et al. | |
| 2016/0166335 A1 | 6/2016 | Roger et al. | |
| 2017/0056086 A1 | 3/2017 | Kostrzewski et al. | |
| 2017/0138770 A1 | 5/2017 | Scholl et al. | |
| 2017/0360493 A1 | 12/2017 | Zucker et al. | |
| 2018/0147018 A1 | 5/2018 | Crawford et al. | |
| 2018/0280147 A1 | 10/2018 | McGahan et al. | |
| 2018/0289408 A1 | 10/2018 | McGahan et al. | |
| 2018/0289491 A1 | 10/2018 | McGahan et al. | |
| 2018/0301213 A1 | 10/2018 | Zehavi et al. | |
| 2019/0029737 A1 | 1/2019 | Wall et al. | |
| 2019/0209080 A1 | 7/2019 | Gullotti et al. | |
| 2019/0231435 A1 | 8/2019 | Zucker | |

FOREIGN PATENT DOCUMENTS

| | | |
|---|---|---|
| WO | WO 2011/134083 | 11/2011 |
| WO | WO 2012/062464 | 5/2012 |
| WO | WO 2015/114119 | 8/2015 |
| WO | WO 2019/043426 | 3/2019 |
| WO | WO 2019/185757 | 10/2019 |

OTHER PUBLICATIONS

Partial European Search Report for European Patent Application No. 15866361.7, dated Jul. 12, 2018, 12 pages.

International Search Report and Written Opinion for International (PCT) Patent Application No. PCT/IL2017/050699, dated Sep. 25, 2017, 11 pages.

Official Action for U.S. Appl. No. 15/533,037, dated Apr. 15, 2019, 7 pages.

Notice of Allowance for U.S. Appl. No. 15/533,037, dated Sep. 30, 2019, 5 pages.

Official Action for U.S. Appl. No. 16/312,296, dated Jan. 27, 2020, 7 pages.

Extended European Search Report for European Patent Application No. 17814903.5, dated Feb. 13, 2020, 11 pages.

Official Action for European Patent Application No. 15866361.7, dated Jun. 17, 2022, 4 pages.

Official Action for European Patent Application No. 15866361.7, dated Feb. 9, 2021, 6 pages.

Official Action with English Translation for China Patent Application No. 201780050056.X, dated Jan. 6, 2021, 12 pages.

Notice of Allowance for U.S. Appl. No. 16/312,296, dated Jul. 20, 2020, 6 pages.

* cited by examiner

SHAPER FOR VERTEBRAL FIXATION RODS

CROSS REFERENCE TO RELATED APPLICATIONS

This application is a continuation of U.S. patent application Ser. No. 15/533,037, filed on Jun. 5, 2017 and entitled "Shaper for Vertebral Fixation Rods," which is a national stage application under 35 U.S.C. § 371 of PCT Application No. PCT/IL2015/051182, having an international filing date of Dec. 4, 2015, which designated the U.S., and which claimed the benefits of and priority under 35 U.S.C. § 119(e) to U.S. Provisional Application Ser. No. 62/087,314, filed on Dec. 4, 2014, entitled "Shaper for Vertebral Fixation Rods." The entire disclosures of each of the foregoing references is hereby incorporated herein by reference.

FIELD OF THE INVENTION

The present invention relates to the field of the shaping of rods used for the fixation of vertebrae in spinal fusion treatment, and their use in robotically directed surgery, especially shaping performed using information obtained from pre-operatively generated images of the surgical site and intraoperative updates.

BACKGROUND OF THE INVENTION

When performing surgery to insert vertebral fixation rods for spinal fusion, there is a need to ensure that the fusion rod is passed accurately between the tulips of the pedicle screws, before the screws are tightened onto the rod. This can be a problematic task since the spine may be severely deformed in a scoliotic patient, and even in a non-scoliotic patient, adjacent vertebrae generally have differing protrusion heights and are not linearly aligned because of the natural spinal lordosis. Reference is made to FIG. 1 which illustrates such a typical vertebral fixation rod implementation, in which the rod 11 had been given a curvature to match the lordosis curvature of the spine 10. In currently used procedures, the surgeon generally bends the fusion rod during the operation, typically using manual tools, so that it matches the positions of the tulips 12 of the pedicle screws, using his/her visual judgment in order to ensure that the rod fits accurately between the heads 12 of the various screws. However this procedure is prone to inaccuracies and since a typical fusion rod is intended to be a high strength component and is generally made of titanium or stainless steel and is typically 5 mm in diameter, the surgeon often has to exert considerable force using pliers to bend the rod appropriately during connection, in order to ensure that the rod fits without exerting undue pressure on the patient's vertebrae.

In US Patent Application Publication No. 2005/0262911 to H. Dankowicz et al, for "Computer Aided Three-Dimensional Bending of Spinal Rod Implants, other Surgical Implants and other Articles, Systems for Three-Dimensional Shaping, and Apparatuses Therefore", there is described a computer aided system for bending an implantable rod three-dimensionally, which is especially useful for pre-surgical formation of implantable spinal rods. Such a system may also use imaging performed intraoperatively on the surgical site, especially to determine the position of pedicle screw heads (tulips) to which the rod is to be attached, in order to determine the shape of the rod to be formed. However, in order to perform intra-operative bending of the rod to match the desired shape in 3D, this system requires the generation of additional images during the procedure, which subjects the patient and possible also the medical staff, to additional radiation exposure.

Therefore, there is a need for an apparatus and procedure which will enable the surgeon to accurately and easily shape a vertebral fixation rod during the surgical procedure, without the need for additional imaging to determine the shape the rod has to be given.

Additionally, although such rod assemblies may be used to fuse two adjacent vertebrae, there are often cases of scoliosis and severe deformities where the region of the spine to be treated may include even 10 or more vertebrae. Such a long construction may be used to rigidly connect all the vertebrae within the desired range, but in certain cases there is no need to fuse all the levels and some vertebra should not be fused together in order to preserve their relative motion. Hence there is also a need for a rod that poses different compliances at different points in accordance with the fusion or dynamic stability needs of the spine.

There therefore exists a need for such devices and methods which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems for rod bending for specific use in robotic spinal surgery, which enables the production on site in the operating room of a fusion rod correctly bent to match the shape required to accurately pass through the tulips on the heads of the pedicle screws, using data generated by the positional information provided to the robot by the surgeon's preoperative plan, augmented if necessary by data feedback provided by the robot control system of any deviations encountered intraoperatively in execution of the surgeon's preoperative plan. In a typical robotic spinal surgical procedure, the surgeon's preoperative plan is generally based on images of the patient's spine generated preoperatively, on the basis of which the surgeon plans exactly where the pedicle screws are to be inserted, at what orientation and to what depth. The surgical robotic system can then direct the robot in all three dimensions such that the drilling position and orientation is adapted to enable the screw hole to be drilled exactly in the position and orientation determined by the surgeon's preoperative plan. Furthermore the three-dimensional nature of the preoperative plan also enables the determination of the extent of protrusion of each screw in the AP direction relative to the patient's spine. In those robotic systems where the drilling itself is performed by a robotic tool, the feedback provided by the robot control system during the drilling operation can provide additional data regarding the extent of any deviation from the surgeon's preoperative plan. This could occur for example when the surgeon decides intraoperatively on a different trajectory or even to skip screws on one vertebra, in which case, the robot will be commanded to perform this alternative procedure, and these instructions will therefore also be relayed to the control system of the rod-bending machine.

The data stored in the robotic control memory includes information regarding the exact position of the pedicle screw heads, both in the lateral and AP directions. This coordinate information can thus be used in a rod bending apparatus, using for instance controlled plungers, to deform the rod in the directions required, such that it matches the coordinate set required by the positions of the heads of the pedicle screws. The plungers can most conveniently be motorized, though other drive methods may also be used, and should be equipped with an encoding mechanism for defining their position. Alternatively, the information regarding the extent of bending required could be obtained by image processing of X-ray images obtained of the spine of the patient after the pedicle screws have been inserted. The output of this image processing procedure could be the set of co-ordinates in three dimensions through which the rod passes through. Alternative bending machine configurations can also be used.

If the procedure is being performed using a navigation or a tracking system to define the position and orientation of the pedicle screw placements, an alternative source for the input data regarding the position of the pedicle screw heads could be provided by the navigation or tracking system itself. This data could be provided either by means of a touch probe which is directed onto the pedicle screw heads, or by means of position emitters fitted directly on the surgical tool or its tool guide. The control system of such a system is able to transfer the positional data directly to the control system of the rod bending equipment, to ensure that the desired shape of the rod is generated.

Additionally, the rod bending apparatus could also be equipped with a facility for thinning down the rod at predetermined locations along its length, at which locations it is desired to maintain a level of flexibility between vertebrae, instead of fixating them.

There is thus provided in accordance with an exemplary implementation of the devices described in this disclosure, a method for shaping an intervertebral connection rod for use in a computer assisted spinal stabilization procedure, the method comprising:
(i) providing a surgical plan based on preoperative images of a patient's spine, the plan defining the position and orientation of pedicle screws whose insertion into the patient's vertebrae is to be performed with the assistance of either a robotic system or a navigation system,
(ii) generating from the robotic or navigation system, positional data incorporating the co-ordinates of the points at which the rod sits correctly in each desired pedicle screw head,
(iii) inputting the positional data to the control system of a rod shaping system, the system adapted to use the positional data to bend a rod inserted therein, such that it adopts a shape that will sit correctly in the desired pedicle screw heads, and
(iv) actuating the system to generate a correctly shaped rod for use in the spinal stabilization procedure.

In such a method, the robotic system may be adapted to insert the pedicle screws, and the method may further comprise the step of adjusting the positional data according to any deviation from the preoperative surgical plan of the final position of the pedicle screw insertion, as determined by the robot system.

According to a further implementation of the above described methods which use a navigation system, the navigation system is used to define the position of the pedicle screw heads by means of a touch probe. Alternatively, the navigation system may be used to define the position of the pedicle screw heads by means of reference markers either on the pedicle screw heads, or on a surgical tool adapted to drill a vertebral hole.

In any of the above described methods, the rod-shaping system may comprise a plurality of plunger pistons disposed laterally to a cavity in which the rod is clamped, and wherein the positional data is used to move the plunger pistons such that they bend the rod to a shape in accordance with the positional data. Such a method may further compromise the rotation of the rod, such that the plurality of plunger pistons can shape the rod in three dimensions. Alternatively, the plurality of pistons may be arranged in more than one plane such that the rod can be shaped in three dimensions without being rotated in the cavity.

According to yet another implementation of the above described methods, the rod shaping system may further comprise a rod thinning module, adapted to reduce the cross-sectional area of the rod at predetermined locations, such that the rod has increased flexibility at the predetermined locations. In such an implementation, the rod thinning module should be able to adapt the cross sectional dimension of the rod in different planes according to clinical need. In either of these cases, the rod thinning module may reduce the cross sectional dimension of the rod by means of indentations generated in the rod at the predetermined locations. In that method, the indentations may be generated by appropriately shaped plunger pistons.

As an alternative to the use of plunger pistons, the rod thinning module may reduce the diameter of the rod by means of mechanical removal of material from the rod at the predetermined locations. That mechanical removal of material may be performed by a controlled milling action.

Additionally, alternative implementations of methods for generating an intervertebral connection rod for use in a dynamic spinal stabilization procedure in a subject, may further involve:
(i) providing a surgical plan of a patient's spine, the plan defining the desired shape of the intervertebral connection rod in three dimensions, and defining vertebrae between which dynamic mutual motion is to be maintained,
(ii) using a rod shaping system to generate the intervertebral connection rod having the desired shape defined by the surgical plan, and
(iii) using the rod-shaping system to reduce the cross-sectional area of the rod at rod locations corresponding to regions falling between the vertebrae when the rod is attached to the subject, such that the rod has increased flexibility at the regions.

In such a method, the surgical plan may be based on preoperative images of the subject.

Still other example implementations involve a system for generating an intervertebral connection rod for use in a dynamic spinal stabilization procedure in a subject, the system comprising:
(i) clamps for holding the rod in the system,
(ii) a bending mechanism for applying predetermined bends to the rod at preselected longitudinal and azimuthal positions such that the rod is shaped in accordance with a surgical plan, and
(iii) at least one rod thinning element disposed such that the cross section of the rod can be reduced at predetermined locations along the length of the rod.

In such a system, the bending mechanism may comprise a set of adjustable rod-bending elements, disposed in positions that enable the elements to apply predetermined bends to the rod at preselected longitudinal and azimuthal positions such that the rod is shaped in accordance with a surgical plan. Alternatively, the bending mechanism may comprise a rotatable chuck for gripping the rod, and a controlled bending mandrel adapted to apply a lateral force on the rod at a point distanced from the chuck. In any such systems, the surgical plan may be based on preoperative images of the subject.

BRIEF DESCRIPTION OF THE DRAWINGS

The present invention will be understood and appreciated more fully from the following detailed description, taken in conjunction with the drawings in which.

DETAILED DESCRIPTION

Figure 1:
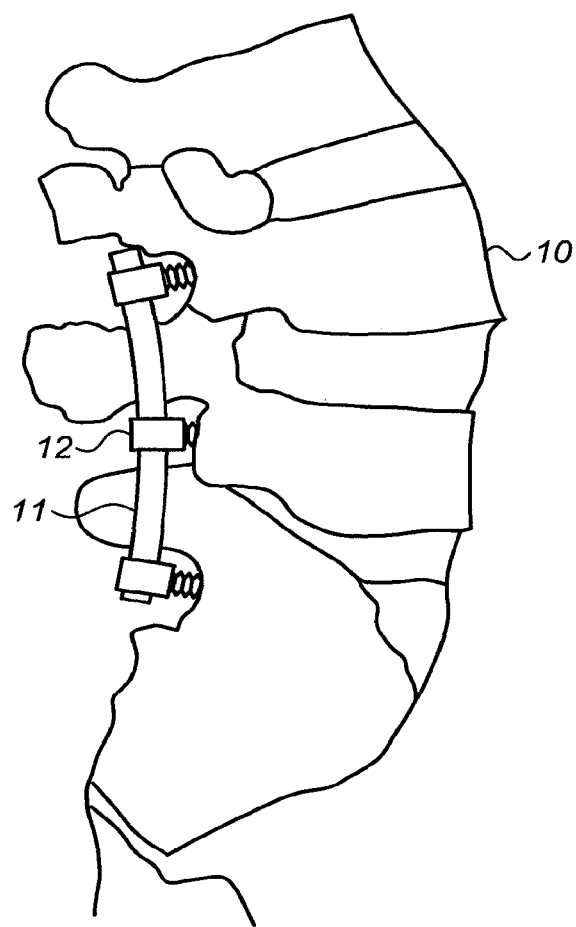
FIG. 1 illustrates a typical vertebral fixation rod implementation, in which the rod had been given a curvature to match the lordosis curvature of the spine.
Figure 2A:
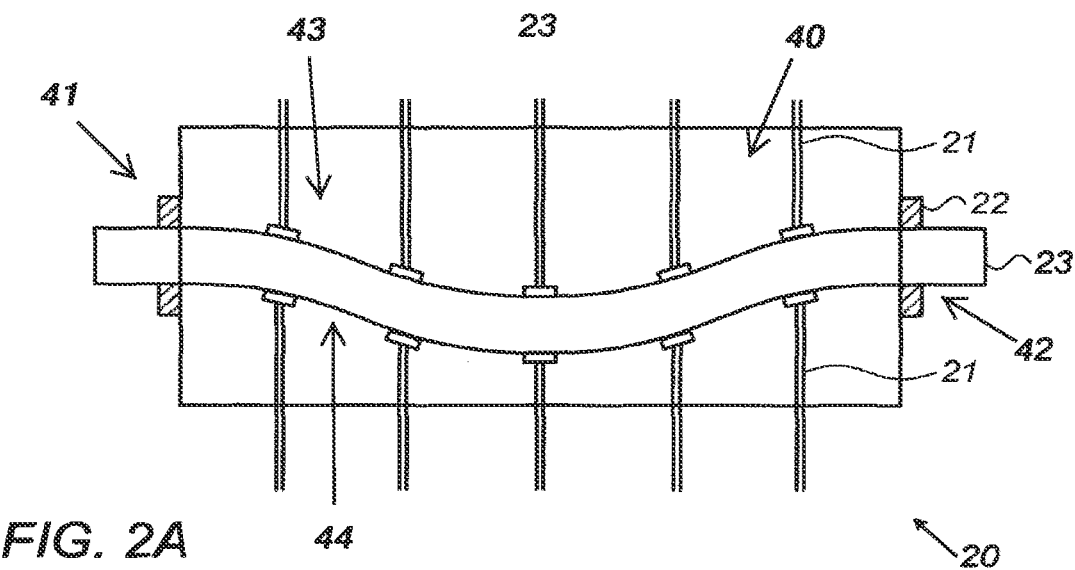
FIG. 2A illustrates schematically a plan view of a rod shaping apparatus, using mechanical plungers or pistons for bending the rod.

Reference is now made to FIG. 2A, which illustrates schematically a plan view of a rod shaping apparatus 20, using mechanical plungers or pistons 21 for shaping the rod. The rod 23 is firmly held in end clamps 22, which may be rotatable to enable three-dimensional bent shapes to be executed. The plungers or pistons 21 may be driven by hydraulic or pneumatic cylinders, or by electric motors (none of which are shown in FIG. 2A), or by any other motion impartation device that can provide sufficient force to bend the rod as required. In the exemplary apparatus shown in FIG. 2A, the rod-bending process in the plane shown is performed by sets of plungers or pistons disposed between a first end 41 and a second end 42 opposite the first end 41 and are also disposed laterally to a cavity 40 of the rod shaping apparatus 20. The sets of plungers or pistons are also arranged opposite to each other and secured to one of a first side 43 or a second side 44, such that good control is achieved of the bending process, and the bending can be achieved in either direction of concavity. However, it is to be understood that a bend in any direction can also be achieved by having the plunger or piston oriented only at the intended concave side of the bend to be produced, and by applying force to the rod from that direction only.

In order to achieve a three-dimensionally shaped rod, as will be required when the patient has any significant extent of scoliotic deformation to add to the natural lordosis curvature, the end clamps 22 may be constructed to be rotatable, and the bends applied in the appropriate plane by the plungers or pistons as the rod is rotated to each appropriate azimuthal angle. Alternatively, a static rod clamp may be used, in which case sets of plungers or pistons are disposed at different azimuthal angles about the axis of the rod, such that the three dimensional shape can be generated with the rod clamped statically.

Figure 2B:
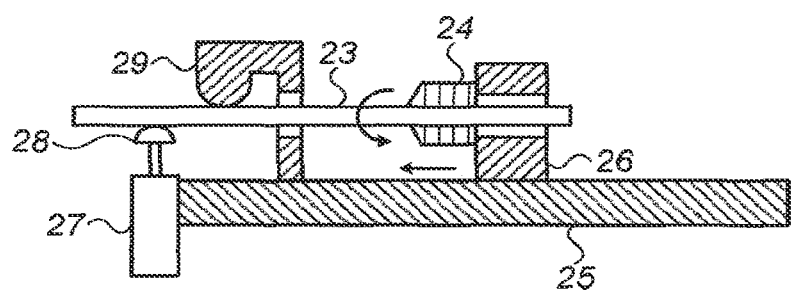
FIG. 2B shows a prior art press bending rod shaping apparatus.

Reference is now made to FIG. 2B, which illustrates schematically a plan view of another typical rod shaping apparatus, which may also be used in the implementation of the methods and systems of the present disclosure. Such bending machine configurations have been known for a long time, and one such example is shown in the above referenced US patent Application Publication No. 2005/0262911. In FIG. 2B, the rod 23 is held in a rotatable clamping chuck 24, mounted on a sliding block base 26, which can move the rod longitudinally along the linear machine base 25. The bending process takes place by applying pressure, such as by means of a hydraulic cylinder 27, to a push die 28, which forces the tube 23 to bend around the forming die 29, which has a radiused contact face to form a smooth curve. The position in the rod of the bend or bends is controlled by the longitudinal position of the sliding base block. Rotation of the rod in the rotatable chuck 24 enables a rod to be formed with three-dimensional curves.

Figure 3:
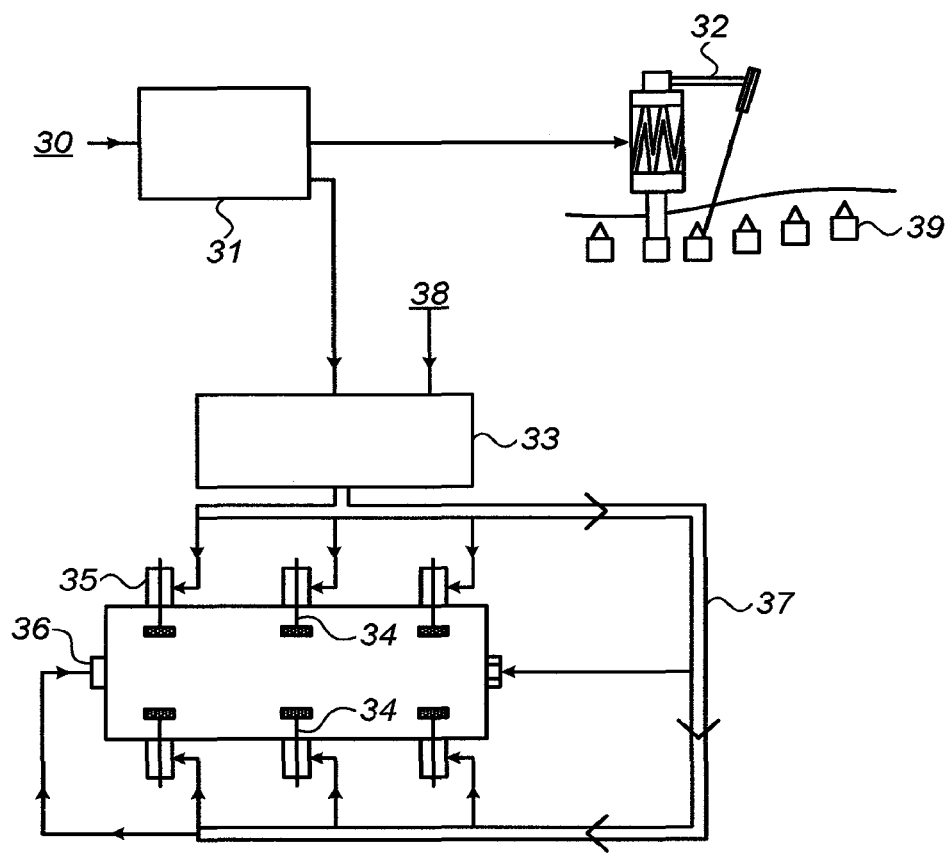
FIG. 3 illustrates how the robot control provides inputs to the plunger control of the rod shaping apparatus of FIG. 2A, so that the rod is shaped to the desired form.

Reference is now made to FIG. 3 which illustrates how the robot control provides inputs to the plunger control 33 of the rod shaping apparatus, so that the rod is shaped to the desired form. The surgical procedure of defining the position and orientation of the pedicle screws and their associated connection rods is generally performed by the surgeon in a surgical plan 30 generally obtained on the basis of preoperative three dimensional image sets, such as CT or MRI images of the region of interest. The surgical plan is used to define the robot pose to be adopted for the drilling of each pedicle screw hole. In some cases, the control system also supervises the drilling operation to form the hole and to screw in the pedicle screws to the required maximum torque to ensure firm insertion. The required information is extracted from the surgical plan 30 and is input to the robot control system 31, to instruct the robot 32 to perform the desired motions to align the surgical tool as required for the process to be performed on the subject's vertebrae 39, such as the drilling of holes for pedicle screws. In addition to providing instructions to activate the robotic motion, the robot controller 31, or an additional control module for extracting co-ordinate information from the surgical plan, inputs location information to the rod shaping apparatus control module 33. An information bus 37 conveys this information, advantageously in the form of a set of motions which each of the shaping pistons or plungers 34 must perform, to servo-controlled actuators 35 to move the plungers or pistons in order to bend the rod (not shown) clamped in the rod shaping apparatus 33 to the desired shape. In addition, in those implementations where the rod is also rotated to provide three-dimensional shaping, commands are also conveyed through the control bus 37 to the rod rotation servo motor or motors 36. By this means, the rod shaping system is able to automatically produce a fixation rod, correctly bent to the shape required for use according to the initial surgical plan 30, without the need for the surgeon to perform any manual operations on the rod during the surgery, in order to adapt it to match the exact positions of the pedicle screw heads.

FIG. 3 shows the implementation of the methods of the present disclosure on a rod-shaping machine having plunger bending action, such as that of FIG. 2A, but it is to be understood that these methods can also be applied to any other sort of controllable bending machine, such as that shown in FIG. 2B, with the appropriate commands output from the shaping controller 33 being directed at the longitudinal motion drive, the bending die position actuator, and the rotational position of the clamping chuck.

Furthermore, in installations where the robot also performs controlled insertion of the pedicle screws, a feedback signal from the robot defining the exact position into which each pedicle screw was inserted, can be used to input further information to the shaper controller, for providing any corrections needed to the bending profile, for instance, in the event that the physiological conditions of the bone were such that the pedicle screws were not inserted to the insertion level requested by the surgical plan, or in the event that the surgeon makes changes intraoperatively to the plan, as mentioned hereinabove. In addition, there is shown in FIG.

an additional and alternative input 38 to the shaper controller from a navigation or a tracking system (not shown).

The above description is applicable to situations where fusion is to be applied to all of the desired section of the patient's spine. However there are many situations in which, because parts of the spinal region being treated may clinically be preferred to have a level of natural flexibility, fusion is not required between all of the adjacent vertebrae of the patient's spine. However, instead of using separate sections of fusion rods excluding those vertebrae sections where fusion may not be required, it may be simpler and more advantageous to use a single rod (generally one on each side of the spine) in order to cover the entire section of the spine to be treated. Moreover, in order to achieve dynamic spinal stabilization between some vertebrae, some rigidity of the rod may be needed between those vertebrae, and this would be missing if two separate sections of rods were to be used. In such situations, some sections of the rod structure have to remain more flexible, such as in locations where the disc is still functional, while other sections of the rod have to maintain their stiffness to assist in providing complete fusion. In order to achieve this structure, at those locations of the patient's spine where some flexibility is desired, the rods can then be provided with thinned sections between the pedicle screw locations. The thinning of the rod can be achieved either by shaving or machining off some of the material of the rod in the region where increased flexibility is desired, or by using the same plungers to generate one or more dimples in the surface of the rod to reduce its thickness, and hence to increase its compliance, at that point. This can be achieved by actuating two opposing plungers operating against each other to thin the rod down in the space between the plungers. This thinning process may be applied either to a pair of rods on either side of the spine, or on a single rod positioned on one side of the spine. The latter procedure is often used in minimally invasive cases, where the use of one rod minimizes the number of skin incisions. Also, if a given compliance between non-fused vertebra is to be maintained in dynamic stabilization, then only one rod with variable rigidity may be preferable.

Instead of plunger generated thinned segments, a miniature controlled milling cutter (not shown) can alternatively be applied to the rod at the relevant positions either to reduce the diameter of the rod, thus increase its flexibility in all orientations, or to generate an asymmetric radial dimension to increase flexibility in a predetermined radial direction, as now explained.

The flexibility is generally applied isotropically, by thinning down the rod uniformly in essentially all azimuthal angles. However, there may be pathological situations in which flexibility is to be maintained in one particular plane of the spine, while rigidity is required another plane. This can be achieved by aligning the direction of the flexibility to match what is desired by the physiological situation of the patient's spine. This can be performed by changing the Moment of Inertia (MOI) of the rod in one plane relative to its orthogonal plane, by applying the thinned out section in one azimuthal plane relative to the rod's axis, but not in the other plane. The desired plane can be selected either by use of a rod shaping system having pistons or plungers aligned at a number of azimuthal angles around the rod and by applying the plungers appropriately, or by rotating the rod so that a single or a pair of oppositely located shaping plungers at a fixed azimuthal angle are aligned in the plane where the flexibility is to be applied. Alternatively, a miniature controlled milling cutter can be applied to the rod at the relevant positions and at the relevant azimuthal angles.

Figure 4:
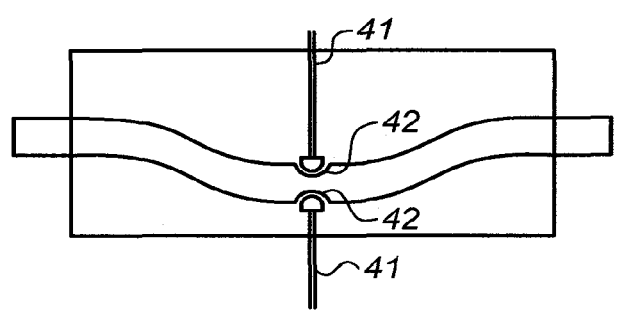
FIG. 4 illustrates a thinning operation being performed using the apparatus shown in FIG. 2A with a pair of oppositely disposed piston plungers.

Reference is now made to FIG. 4 which illustrates one example of how such a thinning operation can be performed using the apparatus shown in FIG. 2A. The exemplary implementation shown in FIG. 4 uses a pair of oppositely disposed piston plungers 41 with mushroom shaped heads which generate indentations 42 on diametrically opposite points of the rod's surface. The indentations essentially thin the rod down. Alternatively, the above mentioned miniature milling cutter could equally well be used. In the case of classic die bending operations, such as in FIG. 2B, the mechanical miniature milling cutter can be positioned at any suitable position along the longitudinal length of the machine. In all cases of thinning, care must be taken not to weaken the rod to a point at which there is danger that it will break due to material fatigue.

Although the above described system has been described with reference to the generation of correctly bent fixation rods for use in spinal fusion using pedicle screw attachment, it is to be understood that the systems are not limited to this particular application, but can be used for bending and shaping orthopedic inserts where the shaping is performed intraoperatively, and where the shape is generally predefined by means of an image-generated preoperative surgical plan.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

What is claimed is:

1. A rod-shaping system, comprising:
 a rod-shaping device, comprising:
  a housing comprising a first end, a second end opposite the first end, a first side, and a second side opposite the first side, the first side and the second side extending between the first end and the second end;
  a pair of clamps for gripping an intervertebral connection rod, one of the pair of clamps disposed at the first end and another of the pair of clamps disposed at the second end, the pair of clamps aligned on a common axis; and
  a plurality of selectively adjustable plungers, each of the plurality of selectively adjustable plungers secured to one of the first side or the second side, the plurality of selectively adjustable plungers configured to generate bends in the intervertebral connection rod by extending to apply a lateral force to the intervertebral connection rod gripped by the pair of clamps at preselected longitudinal positions along the intervertebral connection rod; and
 a control system that:
  receives location information about a position and orientation of a plurality of pedicle screws in a subject's vertebrae, each of the plurality of pedicle screws comprising a pedicle screw head;
  generates, from the location information, positional data comprising co-ordinates of points corresponding to a location of the each pedicle screw head; and
  causes the rod-shaping device to bend the intervertebral connection rod gripped by the pair of clamps, based on the positional data;

wherein the location information is based on feedback signal from a robot that inserts the plurality of pedicle screws into the subject's vertebrae.

2. The system of claim 1, wherein each of the plurality of selectively adjustable plunger is driven by a hydraulic cylinder, a pneumatic cylinder, or an electric motor.

3. The system of claim 1, wherein a first one of the plurality of selectively adjustable plungers is extendable in a first plane and a second one of the plurality of selectively adjustable plungers is extendable in a second plane different than the first plane.

4. The system of claim 1, wherein the location information comprises x-ray images of the subject's vertebrae, the x-ray images showing the plurality of pedicle screws in the subject's vertebrae.

5. The system of claim 1, wherein the location information is based on data from a touch probe or position emitters.

6. The system of claim 1, wherein the control system is further configured to cause the rod-shaping device to rotate the intervertebral connection rod such that the plurality of selectively adjustable plungers bends the intervertebral connection rod in three dimensions.

7. The system of claim 1, wherein causing the rod-shaping device to bend the intervertebral connection rod further comprises selectively actuating at least one pair of oppositely disposed plungers of the plurality of selectively adjustable plungers.

8. The system of claim 1, wherein causing the rod-shaping device to bend the intervertebral connection rod further comprises selectively actuating at least one pair of oppositely disposed plunger of the plurality of selectively adjustable plungers, each plunger of the pair of oppositely disposed plunger comprising a mushroom-shaped head.

9. The system of claim 1, wherein causing the rod-shaping device to bend the intervertebral connection rod comprises selectively actuating the plurality of selectively adjustable plungers, wherein the plurality of selectively adjustable plungers are arranged in more than one plane so as to enable bending of the intervertebral connection rod in three dimensions without rotating the intervertebral connection rod.

10. The system of claim 1, further comprising: a rod thinning device that reduces a cross-sectional area of the intervertebral connection rod at one or more predetermined locations, such that the intervertebral connection rod has increased flexibility at the one or more predetermined locations.

11. The system of claim 10, wherein the control system is further configured to cause the rod thinning module to reduce the cross-sectional area of the intervertebral connection rod at the one or more predetermined locations, thereby changing a moment of inertia of the intervertebral connection rod in a first azimuthal plane relative to an axis of the intervertebral connection rod, but not in a second azimuthal plane orthogonal to the first azimuthal plane.

12. The system of claim 10, wherein the control system is further configured to cause the rod thinning module to reduce the cross-sectional area of the intervertebral connection rod at the one or more predetermined locations by indenting the intervertebral connection rod at the one or more predetermined locations.

13. The system of claim 10, wherein the control system is further configured to cause the rod thinning module to reduce the cross-sectional area of the intervertebral connection rod at the one or more predetermined locations by mechanically removing material from the intervertebral connection rod at the one or more predetermined locations.

14. A rod-shaping system, comprising:
a rod-shaping device, comprising:
a housing comprising a first end, a second end opposite the first end, a first side, and a second side opposite the first side, the first side and the second side extending between the first end and the second end;
a pair of clamps for gripping an intervertebral connection rod, one of the pair of clamps disposed at the first end and another of the pair of clamps disposed at the second end, the pair of clamps aligned on a common axis; and
a plurality of selectively adjustable plungers, each of the plurality of selectively adjustable plungers secured to one of the first side or the second side, the plurality of selectively adjustable plungers configured to generate bends in the intervertebral connection rod by extending to apply a lateral force to the intervertebral connection rod gripped by the pair of clamps at preselected longitudinal positions along the intervertebral connection rod; and
a control system configured to:
receive location information about a position and orientation of a plurality of pedicle screws in a subject's vertebrae, each of the plurality of pedicle screws comprising a pedicle screw head;
generate, from the location information, positional data comprising co-ordinates of points corresponding to a location of the each pedicle screw head;
cause the rod-shaping device to rotate the intervertebral connection rod such that the plurality of selectively adjustable plungers can bend the intervertebral connection rod in three dimensions; and
cause the rod-shaping device to bend the intervertebral connection rod gripped by the pair of clamps, based on the positional data,
wherein causing the rod-shaping device to bend the intervertebral connection rod comprises selectively actuating the plurality of selectively adjustable plungers disposed laterally to a cavity of the rod-shaping device in which the intervertebral connection rod is clamped to bend the intervertebral connection rod based on the location information.

15. The system of claim 14, further comprising: a rod thinning module to reduce a cross-sectional area of the intervertebral connection rod at one or more predetermined locations, such that the intervertebral connection rod has increased flexibility at the one or more predetermined locations.

16. The system of claim 15, wherein the control system is further configured to cause the rod thinning module to reduce the cross-sectional area of the intervertebral connection rod at the one or more predetermined locations by indenting the intervertebral connection rod at the one or more predetermined locations.

17. A rod-shaping system, comprising:
a rod-shaping device, comprising:
a pair of clamps for gripping an intervertebral connection rod, the pair of clamps aligned on a common axis;
a plurality of selectively adjustable plungers, the plurality of selectively adjustable plungers configured to generate bends in the intervertebral connection rod by extending to apply a lateral force to the intervertebral connection rod gripped by the pair of clamps at preselected longitudinal positions along the intervertebral connection rod; and a rod thinning module configured to reduce a cross-sectional area of the intervertebral connection rod at one or more predetermined locations; and a control system configured to:
- receive location information about a position and orientation of a plurality of pedicle screws in a subject's vertebrae, each of the plurality of pedicle screws comprising a pedicle screw head;
- generate, from the location information, positional data comprising co-ordinates of points corresponding to a location of the each pedicle screw head;
- cause the rod thinning module to reduce the cross-sectional area of the intervertebral connection rod at the one or more predetermined locations;
- cause the rod-shaping device to bend the intervertebral connection rod gripped by the pair of clamps, based on the positional data; and
- cause the rod thinning module to reduce the cross-sectional area of the intervertebral connection rod at the one or more predetermined locations, thereby changing a moment of inertia of the intervertebral connection rod in a first azimuthal plane relative to an axis of the intervertebral connection rod, but not in a second azimuthal plane orthogonal to the first azimuthal plane.

* * * * *